United States Patent [19]

Taylor

[11] 4,393,880
[45] Jul. 19, 1983

[54] DEVICE FOR COLLECTING BODY LIQUIDS

[75] Inventor: Glenn N. Taylor, Cary, Ill.

[73] Assignee: The Kendall Company, Boston, Mass.

[21] Appl. No.: 247,499

[22] Filed: Mar. 25, 1981

[51] Int. Cl.³ .............................................. A61F 5/44
[52] U.S. Cl. .................................. 128/760; 128/767;
604/317; 604/322; 248/95; 248/97
[58] Field of Search ............... 128/275, 760, 763, 765,
128/767; 211/71, 74, 79–81; 248/95, 97,
127–128, 311.3, 318; 604/322, 317

[56] References Cited

U.S. PATENT DOCUMENTS

| | | | |
|---|---|---|---|
| 201,653 | 3/1878 | Covert et al. | 248/97 |
| 2,467,866 | 4/1949 | Smolderen et al. | 211/81 X |
| 2,959,386 | 11/1960 | Garth | 248/95 |
| 3,226,070 | 12/1965 | Kurlander | 248/97 |
| 3,655,157 | 4/1972 | Dalton | 248/97 |
| 4,295,619 | 10/1981 | Kulin et al. | 248/95 |
| 4,317,550 | 3/1982 | Hannah | 248/95 |
| 4,332,252 | 6/1982 | Taylor | 248/95 X |
| 4,333,480 | 6/1982 | Villari et al. | 128/767 |

Primary Examiner—Lee S. Cohen
Assistant Examiner—Angela D. Sykes
Attorney, Agent, or Firm—Powell L. Sprunger

[57] ABSTRACT

A device for collecting body liquids comprising, a receptacle having a chamber to receive and collect the body liquids. The device has a stand having a back member, and legs extending from a lower portion of the back member. An upper portion of the stand is connected to an upper portion of the receptacle. The device has an elongated handle member having inner and outer ends, with the inner end of the handle member being connected to the upper portion of the stand.

18 Claims, 27 Drawing Figures

U.S. Patent  Jul. 19, 1983  Sheet 1 of 5  4,393,880
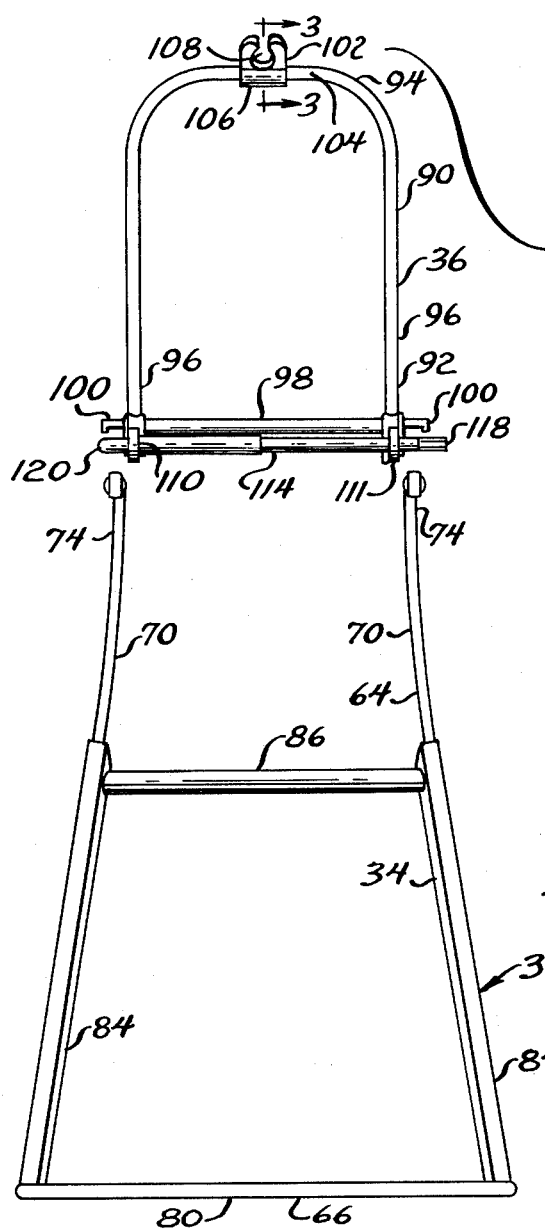
FIG. 1
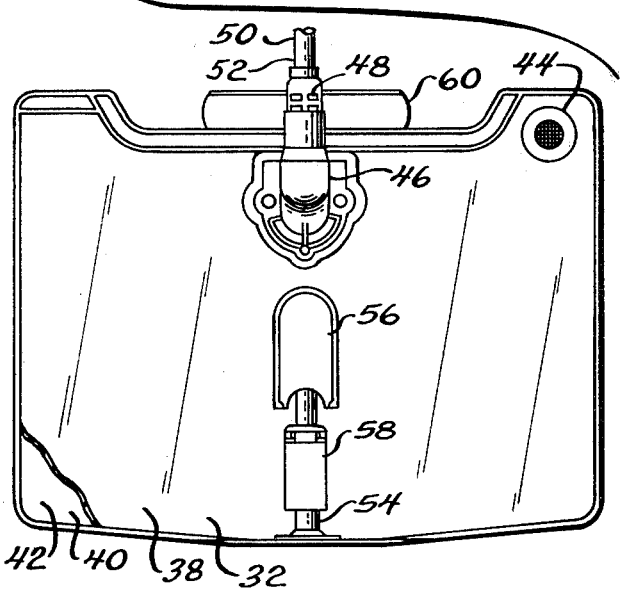
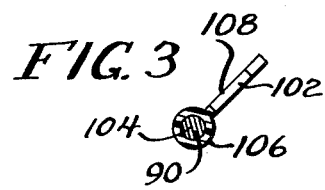
FIG. 3
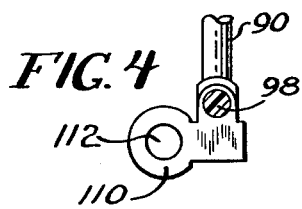
FIG. 4
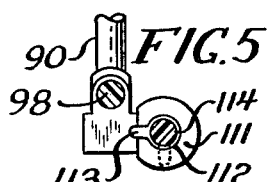
FIG. 5
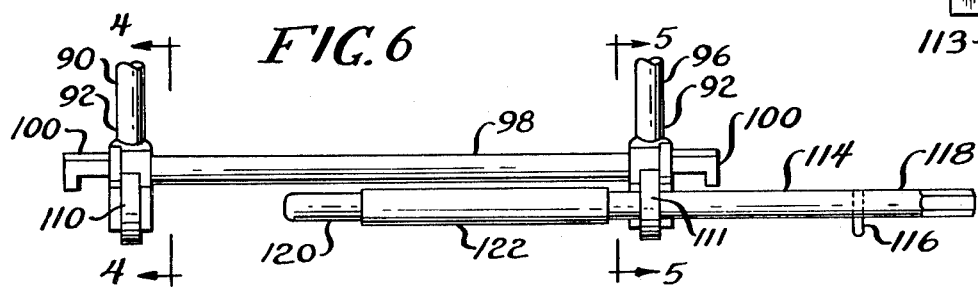
FIG. 6

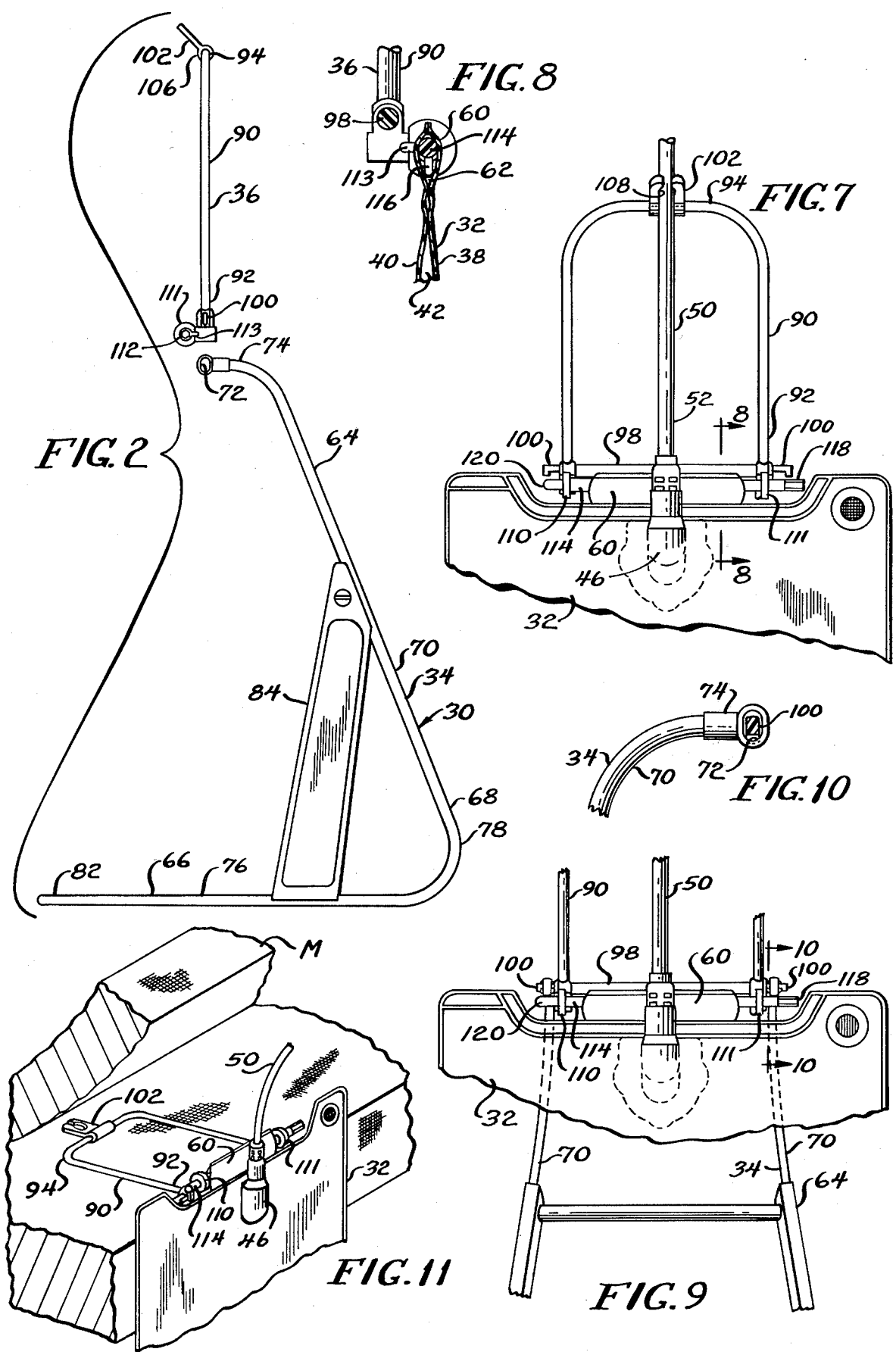

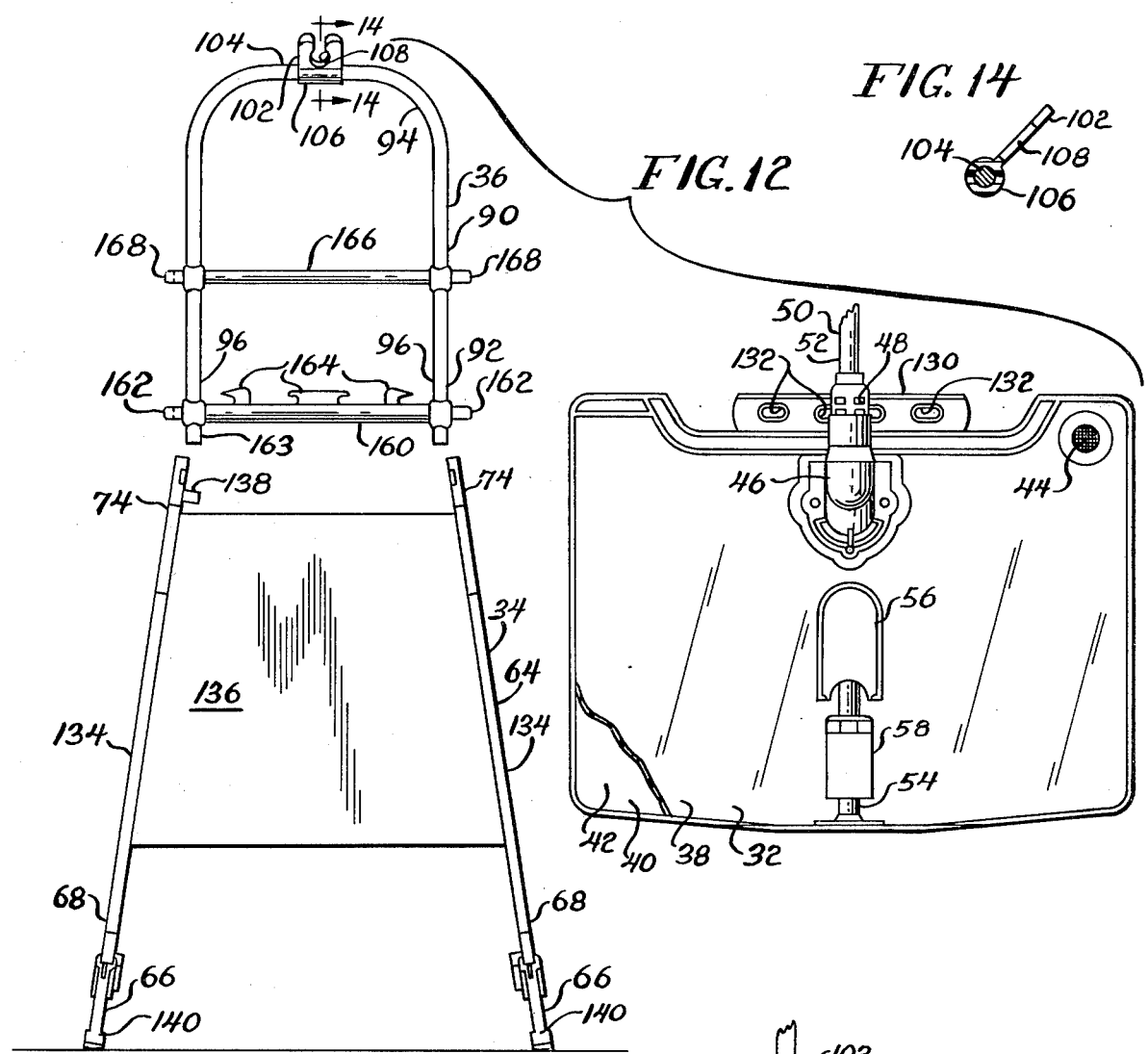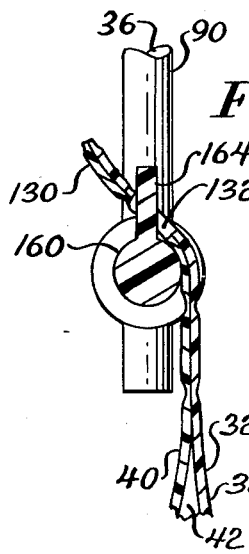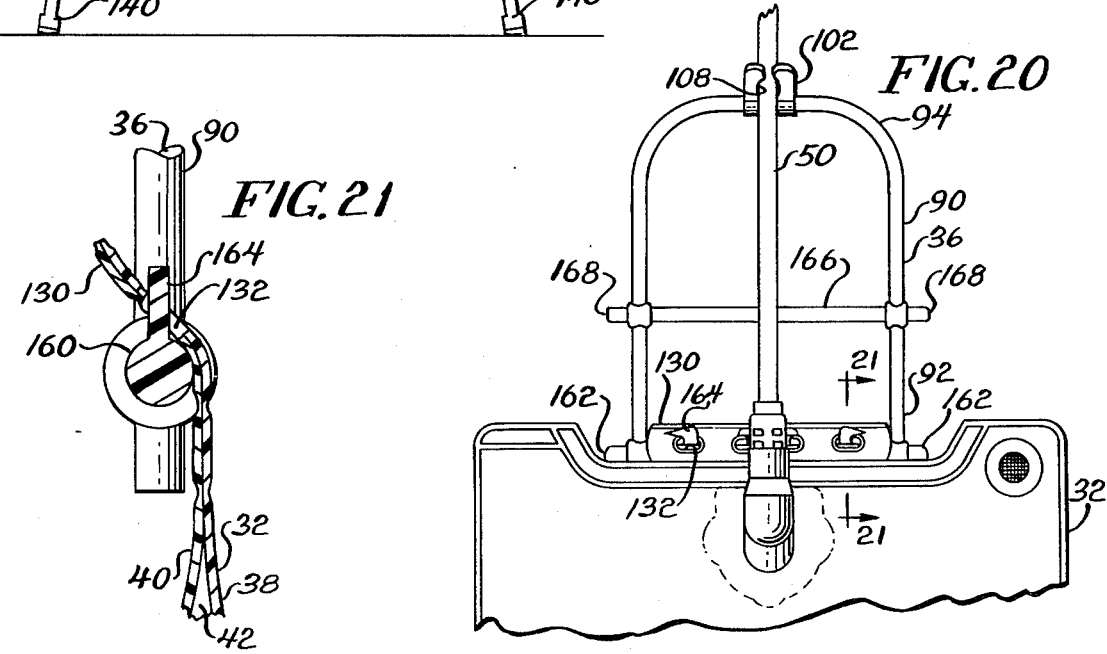

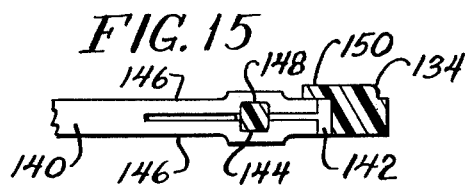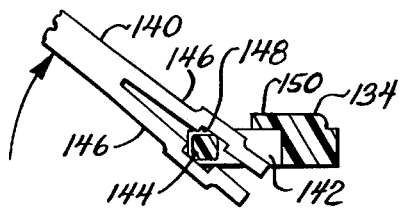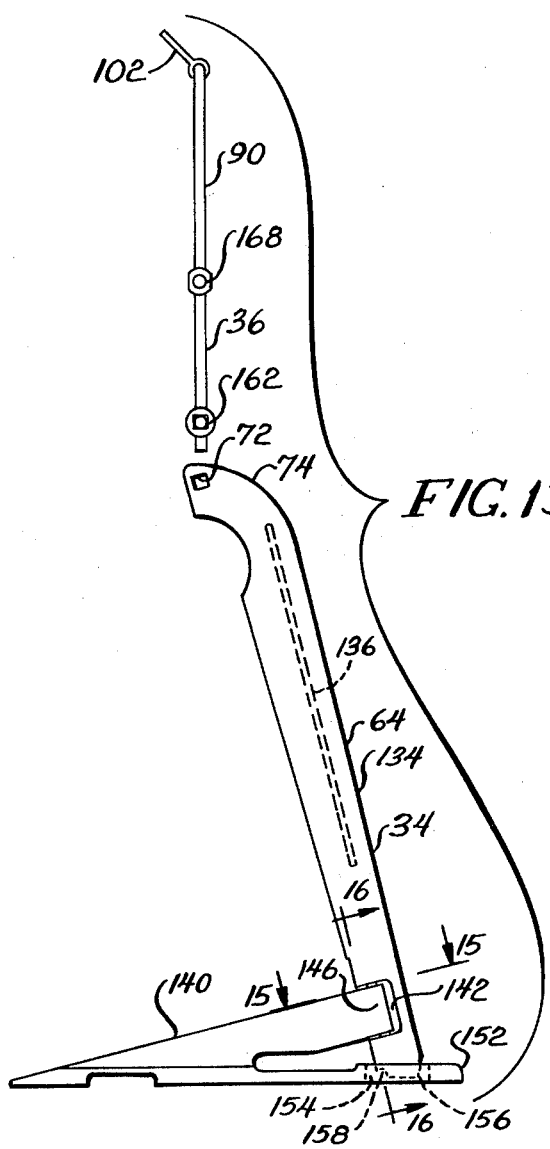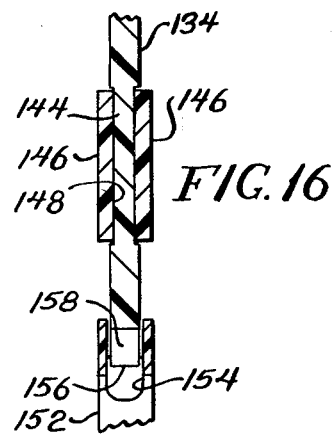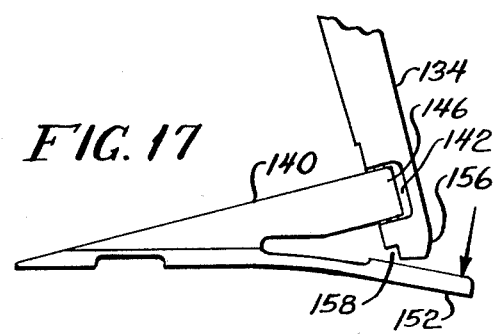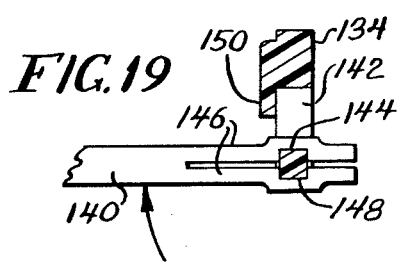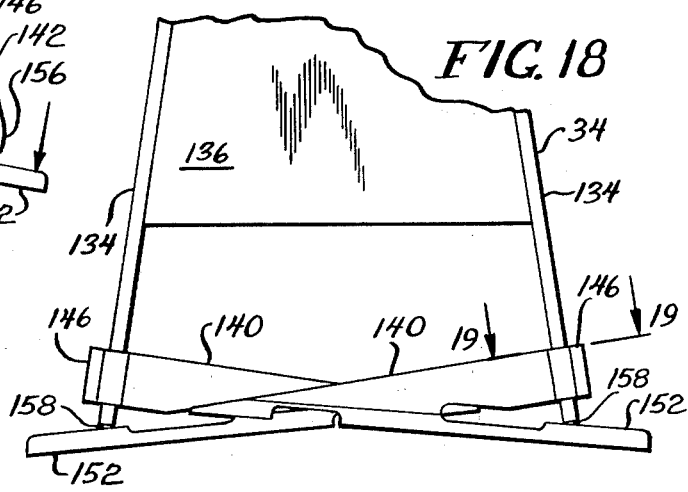

DEVICE FOR COLLECTING BODY LIQUIDS

BACKGROUND OF THE INVENTION

The present invention relates to devices for collecting body liquids.

In the past, liquid drainage devices have been proposed to collect urine from a patient. Such drainage devices may comprise a catheter which is passed through the urethra of the patient, a drainage tube connected to a proximal end of the cathether located outside the patient's body, and a collection bag connected to a downstream end of the drainage tube. In use, urine drains from the bladder through the catheter and drainage tube to the bag for collection therein. Although such devices have operated to drain urine from the patient, various devices were required to secure the drainage bag to the patient's bed, and such devices have deterred the mobility of the patient.

SUMMARY OF THE INVENTION

A principal feature of the present invention is the provision of an improved device for collecting body liquids.

The device of the present invention comprises a receptacle having a chamber to receive and collect the body liquids, and a stand having a back member, and leg means extending from a lower portion of the back member. The upper portion of the stand is connected to an upper portion of the receptacle. The device has an elongated handle member having inner and outer ends. The inner end of the handle member is connected to an upper portion of the stand.

A feature of the present invention is that the stand supports the receptacle in an upright position on the floor adjacent the patient.

Thus, a feature of the present invention is that it is not necessary to secure the receptacle to the bed of the patient.

Another feature of the invention is that the handle member may be utilized by the patient to carry the receptacle about while the receptacle is located on the stand.

Accordingly, a feature of the present invention is that the device facilitates mobility of the patient.

Still another feature of the invention is that the handle member may be placed below a mattress of a bed or a cart with the receptacle supported in an upright position.

Yet another feature of the invention is that the handle member may be placed below a cushion on a wheel chair to support the receptacle in an upright position while the patient moves about in the wheel chair.

Further features will become more fully apparent in the following description of the embodiments of this invention and from the appended claims.

DESCRIPTION OF THE DRAWINGS

In the drawings:

FIG. 1 is a fragmentary front exploded view of a urine collection device of the present invention comprising a receptacle, a stand, and a handle member;

FIG. 2 is an exploded side view of the device of FIG. 1;

FIG. 3 is a sectional view taken substantially as indicated along the line 3—3 of FIG. 1;

FIG. 4 is a fragmentary sectional view taken substantially as indicated along the line 4—4 of FIG. 6;

FIG. 5 is a fragmentary sectional view taken substantially as indicated along the line 5—5 of FIG. 6;

FIG. 6 is a fragmentary plan view on an enlarged scale of a portion of the handle member of FIG. 1;

FIG. 7 is a fragmentary front plan view of the device with the receptacle connected to the handle member;

FIG. 8 is a fragmentary sectional view taken substantially as indicated along the line 8—8 of FIG. 7;

FIG. 9 is a fragmentary front plan view illustrating the receptacle and handle member as attached to the stand;

FIG. 10 is a fragmentary sectional view taken substantially as indicated along the line 10—10 of FIG. 9;

FIG. 11 is a fragmentary perspective view illustrating use of the handle member to support the receptacle beneath the mattress of a patient;

FIG. 12 is a fragmentary front exploded view of another embodiment of the urine collection device of the present invention;

FIG. 13 is a side exploded view of the collection device of FIG. 12;

FIG. 14 is a sectional view taken substantially as indicated along the line 14—14 of FIG. 12;

FIG. 15 is a fragmentary sectional view taken substantially as indicated along the line 15—15 of FIG. 13;

FIG. 15a is a fragmentary sectional view of the device of FIG. 15 in which a leg of the stand is partially rotated from its position in FIG. 15;

FIG. 16 is a fragmentary sectional view taken substantially as indicated along the line 16—16 of FIG. 13;

FIG. 17 is a fragmentary side elevational view illustrating the unlocking of a leg of the stand;

FIG. 18 is a fragmentary front plan view showing legs of the stand as folded inwardly toward a central portion of the stand;

FIG. 19 is a fragmentary sectional view taken substantially as indicated along the line 19—19 of FIG. 18;

FIG. 20 is a fragmentary front plan view of the handle member as connected to the receptacle;

FIG. 21 is a fragmentary sectional view taken substantially as indicated along the line 21—21 of FIG. 20;

DESCRIPTION OF THE PREFERRED EMBODIMENTS

Figure 22:
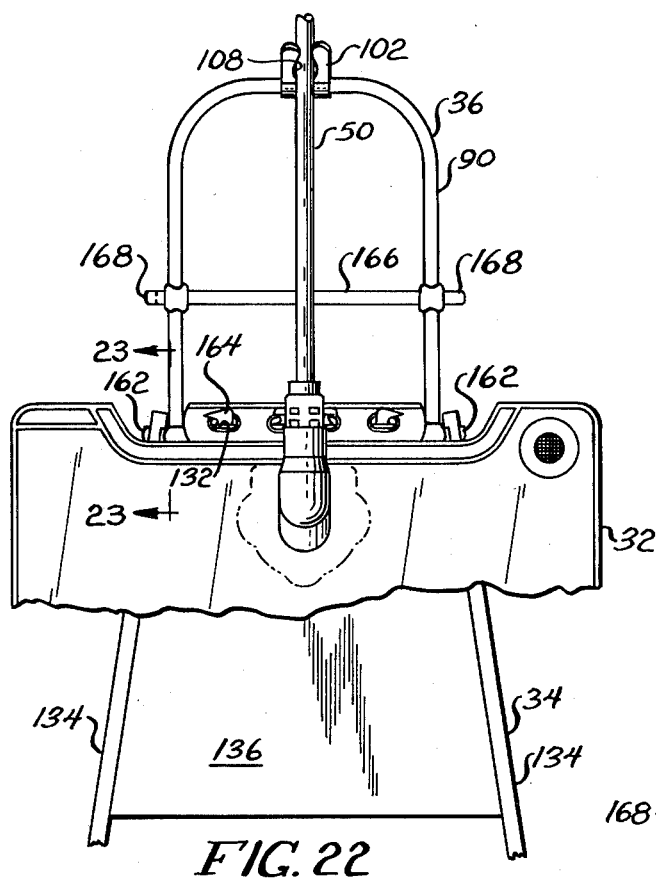
FIG. 22 is a fragmentary front plan view showing the receptacle and handle member as connected to the stand.

Referring now to FIGS. 1-11, there is shown a urine collection device 30 having a collection bag or receptacle 32, a stand 34, and a handle member 36. The receptacle 32 has a front wall 38 of flexible plastic material, and a back wall 40 of flexible plastic material. As shown, the front and back walls 38 and 40 are secured together around their periphery in order to define a chamber 42 intermediate the front wall and back wall 38 and 40.

The receptacle 32 may have a vent 44 of known material, such that the vent 44 communicates between the chamber 42 and the atmosphere. The receptacle 32 has a connector 46 in the form of a drip chamber connected to the front wall 38, such that the connector 46 communicates with the chamber 42 of the receptacle 32. As shown, the connector 46 may have a vent 48 of known material in order to permit passage of air from the atmosphere into the connector 46. The receptacle 32 has a drainage tube 50 with the downstream end 52 of the drainage tube 50 being connected to an upper portion of the connector 46, such that the downstream end 52 of the drainage tube 50 communicates with the chamber 42 through the connector 46. The receptacle 32 has a tubular section 54 connected to the front wall 38 and communicating with the chamber 42. The receptacle 32 has a pocket 56 on the front wall 38 to receive an end of the tubular section 54 in a storage position of the tubular section 54. As shown, a clamp 58 of known type is positioned on the tubular section 54 in order to close the tubular section 54. In use, the tubular section 54 is removed from the pocket 56, and the clamp 58 is opened in order to permit drainage of urine through the tubular section 54. After drainage has been completed, the tubular section 54 is again positioned in the pocket 56 with the clamp 58 closed in order to position the tubular section 54 in the storage position on the receptacle 32. The receptacle 32 also has a sleeve 60 on an upper portion of the receptacle 32, with the sleeve 60 defining a tunnel 62 for a purpose which will be described below.

The stand 34 has a back member 64, and leg means 66 projecting forwardly from a lower portion 68 of the back member 64. The back member 64 comprises a pair of spaced first upright rods 70 having apertures 72 in an upper end 74 of the first rods 70. The stand 34 has a pair of spaced second rods 76 projecting forwardly from a lower end 78 of the first rods 70. Also, the stand 34 has a third rod 80 extending between outer ends 82 of the second rods 76, with the leg means 66 comprising the second rods 76 and third rod 80. As shown, the stand 34 has a pair of reinforcement members 84 extending between the first and second rods 70 and 76, and the stand 34 may have a post 86 extending between upper ends of the reinforcement members 84.

The handle member 36 comprises a U-shaped rod 90 having an inner end 92 and an outer end 94, with opposed ends 96 of the U-shaped rod 90 being connected to a transverse bar 98. In a preferred form, the handle member 36 has a length substantially the length of the receptacle 32, and the length of the handle member 36 may be approximately 7 inches. As shown, the bar 98 has a pair of bosses 100 extending from opposed ends of the bar 98. The handle member 36 has a retaining member 102 pivotally secured to a central portion 104 of the U-shaped rod 90 by a sleeve 106. The retaining member 102 has an aperture 108 for a purpose which will be described below.

The handle member 36 has a pair of spaced ears 110 and 111 extending outwardly from the inner end 92 of the U-shaped rod 90, with the ears 110 and 111 having openings 112 extending therethrough. As shown in FIG. 5, one of the ears 111 has a slot 113 extending through the one ear 111 and being located adjacent the associated opening 112. With reference to FIGS. 1, 2 and 6–8, the handle member 36 also has an elongated rod 114, with the rod 114 having an outwardly directed pin 116 adjacent one end 118 of the rod 114.

In use, the other end 120 of the rod 114 is passed through the opening 112 of the one ear 111, and then the other end 120 of the rod 114 is passed through the tunnel 62 of the receptacle 32, after which the other end 120 of the rod 114 is passed through the opening 112 of the other ear 110. Next, the pin 116 of the rod 114 is passed through the slot 113 in order to position the pin 116 intermediate the ears 110 and 111, with the pin 116 being located adjacent the one ear 111 in order to releasably lock the rod 114 in the ears 110 and 111, as shown in FIG. 7. With reference to FIG. 6, the rod 114 has an enlarged portion 122 which is larger in diameter than the opening 112 in ear 110, such that the enlarged portion abuts against the ear 110 in order to retain the pin 116 adjacent the ear 111. Of course, the opening 112 of ear 111 is larger in diameter than the enlarged portion 122 in order to permit passage of the enlarged portion 122 through the ear 111. In this manner, the handle member 36 is releasably attached to the sleeve 60 of the receptacle 32, with the rod 114 being pivotally received in the tunnel 62. Next, a portion of the drainage tube 50 may be inserted into the aperture 108 of the retaining member 102 in order to retain the drainage tube 50 in place.

The upper ends 74 of the first rods 70 may then be flexed outwardly in order to position the bosses 100 of the handle member 36 intermediate the upper ends 74 of the first rods 70, after which the first rods 70 are released in order to receive the bosses 100 in the apertures 72 of the first rods 70, as shown in FIG. 10. In this manner, the inner end 92 of the handle member 36 and an upper portion of the receptacle 32 are releasably connected to an upper portion of the stand 34. In this configuration, the stand 34 may be positioned on the floor in order to support the receptacle 32 in an upright position at a location adjacent the patient. Thus, the device 30 of the present invention eliminates the need to connect the receptacle 32 to the patient's bed. In addition, the patient may conveniently grasp the handle member 36 and carry the device 30 with him as he moves about, thus increasing the mobility of the patient. If desired, the upper ends 74 of the first rods 70 may be outwardly flexed in order to remove the bosses 100 of the handle member 36 from the apertures 72 of the stand 34, thus leaving the handle member 36 pivotally secured to the receptacle 32. As shown in FIG. 11, the mattress M of a bed or a cart may be lifted from the bed or cart to receive the handle member 36 beneath the mattress M, after which the mattress M is lowered in order to releasably secure the handle member 36 in place beneath the mattress M. In this manner, the receptacle 32 is supported in an upright position by the handle member 36 beneath the mattress M. Alternatively, the handle member 36 may be placed beneath the cushion of a wheel chair in order to releasably secure the receptacle 32 in an upright position on the wheel chair, thus permitting mobility of the patient in the wheel chair while the receptacle 32 is secured in place.

Another embodiment of the present invention is illustrated in FIGS. 12–26, in which like reference numerals designate like parts. In this embodiment, the device 30 has a receptacle 32, a stand 34, and a handle member 36, with the length of the handle member 36 being substantially the length of the receptacle as previously described. In this embodiment, the receptacle 32 is identical to the receptacle 32 previously described in connection with FIGS. 1–11, except that the receptacle 32 of FIGS. 12–26 has a flap 130 at an upper end of the receptacle 32. As shown, the flap 130 has a plurality of spaced slots 132 extending across the flap 130.

The stand 34 has a back member 64, and leg means 66 projecting forwardly from a lower portion 68 of the back member 64. The back member 64 comprises a pair of spaced arms 134, with the arms 134 having apertures 72 adjacent upper ends 74 of the arms 134. Also, the back member 64 has a back plate 136 extending between the arms 134. The back member 64 has an abutment member 138 located adjacent the upper end 74 of one of the arms 134, with the abutment member 138 projecting outwardly from the associated arm 134 at a location adjacent the aperture 72 in the associated arm 134.

The stand 34 has a pair of legs 140 pivotally mounted on the lower portions 68 of the arms 134. The arms 134 have a cut-out 142 adjacent the lower portions 68 of the arms 134, and a pin 144 extending across a forward part of the cut-outs 142. Also, the legs 140 have a pair of spaced flanges 146 defining a bore 148, with the bores 148 receiving the pins 144 to pivotally mount the legs 140 on the arms 134. Thus, the legs 140 are movable between a first forward position, as shown in FIGS. 12 and 13, to a second folded inner position, as shown in FIG. 18, with the legs 140 generally aligned with the back member 64. As shown in FIG. 15, the arms 134 has a stop member 150 adjacent the cut-outs 142 which strike against inner ends of the leg flanges 146 at the first forward position of the legs 140 in order to prevent movement of the legs 140 in an outer direction past the first forward position at which the flanges 146 strike the stop member 150.

With reference to FIGS. 13, and 16-18, the legs 140 have a flexible lower flange 152 having a slot 154 extending vertically through the flanges 152. The arms 134 have a lower protuberance 156 which are received in the slots 154 in order to releasably lock the legs 140 in their first forward position. The legs 140 may be unlocked by flexing the flanges 152 downwardly past the protuberance 156, as shown in FIG. 17, at which time the legs 140 may be pivoted to the second inner position as previously described. The arms 134 also have a notch 158 adjacent the protuberances 156 at the lower end of the arms 134. With reference to FIG. 18, when the legs 140 are folded to the second inner position, the flanges 152 are received in the notches 158 in order to releasably lock the legs 140 at the second inner position. The flanges 152 may be flexed downwardly past the protuberances 156 in order to release the legs 140, and permit movement of the legs 140 to the first forward position. Thus, the legs 140 are movable between the first forward position and a second inner position, and may be releasably locked at both the first forward position and second inner position.

With reference to FIGS. 12 and 13, the handle member 36 comprises a U-shaped rod 90 having an inner end 92 and an outer end 94 in a manner as previously described in connection with the device 30 of FIGS. 1-12. In this embodiment, a retaining member 102 is pivotally mounted on a central portion 104 of the U-shaped rod 90 by a sleeve 106, with the retaining member 102 having an aperture 108 to receive a portion of the drainage tube 50 on the receptacle 32, as previously described.

Opposed ends 96 of the U-shaped rod 90 are connected to spaced portions of a first rod 160, with the first rod 160 having opposed first bosses 162 extending outwardly from opposed ends of the rod 160. As shown, the first rod 160 has a plurality of hooks 164 extending outwardly from the rod 160 for a purpose which will be described below. Also, the U-shaped rod 90 has a second rod 166 connected between the U-shaped rod 90 intermediate the inner end 92 and outer end 94 of the U-shaped rod 90. The second rod 166 has a pair of second bosses 168 extending from opposed ends of the second rod 166. The handle member 36 has a protuberance 163 extending from the inner end 92 of the U-shaped rod 90 at a location adjacent one of the bosses 162.

Figure 23:
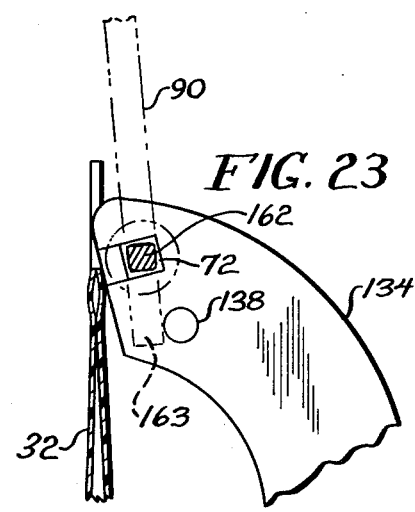
FIG. 23 is a fragmentary sectional view taken substantially as indicated along the line 23—23 of FIG. 22.

In use, the hooks 164 of the first rod 160 are received in the slots 132 of the receptacle flap 130, as shown in FIG. 20, in order to releasably secure the receptacle 32 onto the handle member 36. Next, the upper ends 74 of the arms 134 may be flexed outwardly slightly in order to receive the first bosses 162 intermediate the upper ends 74 of the arm 134, after which the upper ends 74 of the arms 134 may be released in order to pivotally receive the bosses 162 in the apertures 72 of the stand 34, as shown in FIG. 22. As shown in FIG. 23, in this configuration, the protuberance 163 strikes the abutment member 138 of the stand in order to limit forward movement of the handle member 36 relative to the stand 34 at an upright position of the handle member 36. At this time, the legs 140 may be folded to the first forward position, as shown in FIGS. 12 and 13. In this configuration, as shown in FIG. 22, the stand 34 supports the receptacle 32 in an upright position with the legs 140 of the stand 34 being located on the floor adjacent the patient to support the stand 34 in an upright position. Also, in this configuration, the handle member 36 is releasably attached to the receptacle 32, and the drainage tube 50 may be received in the aperture 108 of the retaining member 102 in order to retain the drainage tube 50 in place. Thus, the device 30 may be placed in an upright position on the floor, and the patient may grasp the handle member 36 in order to carry the device 30 about in order to increase the mobility of the patient.

Figure 26:
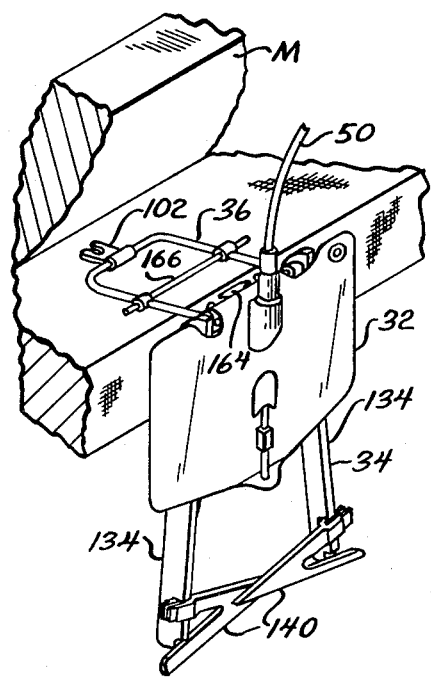
FIG. 26 is a fragmentary perspective view illustrating the handle member as placed beneath a mattress with the stand secured to the device.
Figure 25:
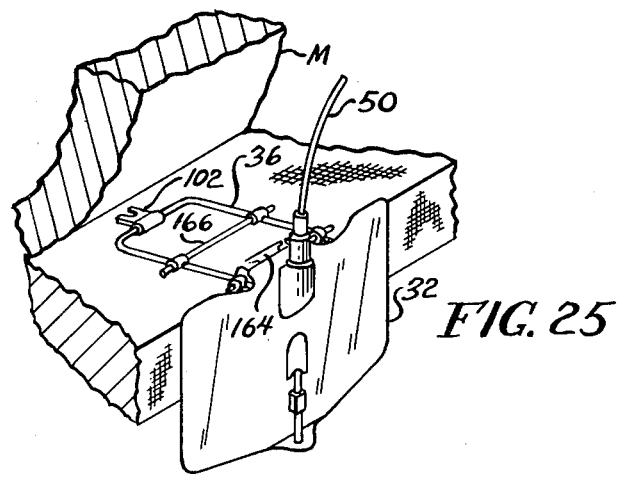
FIG. 25 is a fragmentary perspective view illustrating the handle member as placed beneath a mattress with the stand removed from the device.

If desired, with reference to FIG. 26, the legs 140 may be unlocked and moved to their second inner position, and the drainage tube 50 may be released from the retaining member 102. In this configuration, the handle member 36 may be placed beneath a mattress M of a bed or a cart, and the mattress M may be lowered over the handle member 36 in order to retain the receptacle 32 in an upright position by the mattress M or by a cushion on a wheel chair with the stand 34 being attached to the receptacle 32 and handle member 36. Alternatively, with reference to FIG. 25, the stand 34 may be removed from the receptacle 32, and the handle member 36 may be placed beneath a mattress M in order to support the receptacle 32 in an upright position by the mattress M or by the cushion of a wheel chair with the stand 34 removed from the device 30. Thus, the receptacle 32 may be supported by the side of a patient through use of the handle member 36 whether or not the stand 34 is attached to the receptacle 32.

Figure 24:
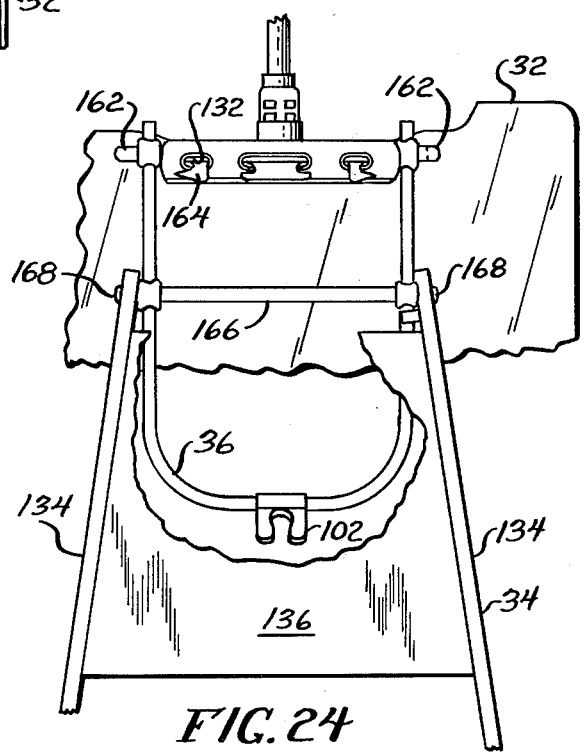
FIG. 24 is a fragmentary rear plan view illustrating the receptacle as connected to the stand in an inverted position of the handle member.

In an alternative configuration, with reference to FIG. 24, the handle member 36 may be inverted relative to the receptacle 32, and the second bosses 168 may be positioned in the aperture 72 of the arms 134. In this configuration, the receptacle 32 is supported by the stand 34 at a higher position relative to the floor on which the stand 34 rests. Alternatively, the handle member 36 may be located above the receptacle 32, and the second bosses 168 may be inserted into the aperture 72 of the arms 134 in order to support the receptacle 32 at a lower position on the stand 34 relative to the floor.

Thus, in accordance with the present invention, the receptacle 32 may be releasably attached to the handle member 36, and the handle member 36 may be connected to the stand 34 in order to support the receptacle 32 in an upright position on the floor while the legs 140 are located at the first forward position. The handle member 36 may be placed beneath a mattress M of a bed or a cart or the cushion of a wheel chair in order to support the receptacle 32 at the side of the patient whether or not the stand 34 is removed from the handle member 36. Also, the receptacle 32 may be supported at varying heights on the stand 34 through use of the second bosses 168 in the apertures 72 of the arms 134, with the handle member 36 being located in an upright or inverted position.

The foregoing detailed description is given for clearness of understanding only, and no unnecessary limitations should be understood therefrom, as modifications will be obvious to those skilled in the art.

I claim:

1. A device for collecting body liquids, comprising:
a receptacle having a chamber to receive and collect body liquids;
a stand having a back member having upper and lower portions, and leg means extending from the lower portion of said back member to support the back member in an upright position; and
means for connecting an upper portion of the back member to an upper portion of the receptacle to support the receptacle in a upright position by the stand, wherein the connecting means releasably attaches the back member to the receptacle, with the connecting means comprising a tunnel in an upper portion of the receptacle, a rod extending through the tunnel, and means for attaching said rod to the back member, wherein the attaching means comprises a pair of spaced apertures in the upper portion of the back member, a pair of spaced bosses removably received in said apertures, a pair of spaced ears connected to said bosses, said ears having openings to removably receive said rod with the tunnel located intermediate said ears.

2. The device of claim 1 including a bar extending between said bosses.

3. The device of claim 1 wherein said rod has an outwardly directed pin, and in which one of said ears has a slot adjacent the opening in the one ear, said slot receiving the pin such that the pin may be passed through the slot to position the pin intermediate said ears at a location adjacent the one ear.

4. The device of claim 1 including an elongated handle member connected to said bosses.

5. The device of claim 4 wherein said handle member comprises a U-shaped rod having opposed ends connected to said bosses.

6. The device of claim 5 wherein said receptacle includes a drainage tube having a downstream end communicating with said chamber, and in which a central portion of the U-shaped rod has a retaining member having an aperture to releasably receive a portion of said drainage tube.

7. The device of claim 6 wherein said retaining member is pivotally mounted on said U-shaped rod.

8. The device of claim 1 wherein said back member comprises a pair of spaced upright first rods having upper and lower ends.

9. The device of claim 8 wherein the upright first rods each have an aperture adjacent an upper end of the rods.

10. The device of claim 8 wherein the leg means comprises a pair of second rods having inner and outer ends extending forwardly from lower ends of the first rods.

11. The device of claim 10 wherein the leg means further comprises a third rod extending between outer ends of the second rods.

12. The device of claim 10 including a pair of reinforcement members extending between the first and second rods.

13. The device of claim 1 wherein said receptacle has a pair of flexible sidewalls defining said chamber.

14. The device of claim 1 wherein the leg means extends forwardly from the back member.

15. A device for collecting body liquids, comprising:
a receptacle having a chamber to receive and collect the body liquids;
a stand having a back member having upper and lower portions, and leg means extending from the lower portion of the back member to support the back member in an upright position;
means for connecting an upper portion of the back member to an upper portion of the receptacle to support the receptacle in an upright position by the stand;
an elongated handle member having inner and outer ends; and
means for pivotally and removably connecting the inner ends of the handle member to the upper portion of the back member.

16. The device of claim 15 wherein the handle member has a length substantially the length of said receptacle.

17. The device of claim 15 wherein the handle member comprises a U-shaped rod.

18. A device for collecting body liquids, comprising:
a receptacle having a chamber to receive and collect the body liquids;
a stand having a back member having upper and lower portions, and leg means extending from the lower portion of the back member to support the back member in a upright position;
means for connecting an upper portion of the back member to an upper portion of the receptacle to support the receptacle in an upright position by the stand;
an elongated handle member having inner and outer ends; and
means for pivotally connecting the inner ends of the handle member to the upper portion of the receptacle.

* * * * *